(12) United States Patent
Kim et al.

(10) Patent No.: US 6,884,882 B1
(45) Date of Patent: Apr. 26, 2005

(54) 2'-DEOXYURIDINE DERIVATIVES AND HYDROGELS FORMED THEREWITH

(75) Inventors: Byeang Hyean Kim, Pohang-si (KR); Sun Min Park, Pohang-si (KR); Yoon Suk Lee, Daejeon (KR)

(73) Assignee: Postech Foundation (KR)

( * ) Notice: Subject to any disclaimer, the term of this patent is extended or adjusted under 35 U.S.C. 154(b) by 0 days.

(21) Appl. No.: 10/833,710

(22) Filed: Apr. 27, 2004

(30) Foreign Application Priority Data

Jan. 7, 2004 (KR) .................. 10-2004-0000975

(51) Int. Cl.[7] ..................... C07H 19/06; C07H 19/073; A61K 31/7072
(52) U.S. Cl. ................. 536/28.53; 536/28.4; 536/55.3; 514/50
(58) Field of Search ............... 536/28.53, 28.4, 536/55.3; 514/50

(56) References Cited

U.S. PATENT DOCUMENTS 5,212,161 A * 5/1993 Moriniere et al. ............ 514/50

* cited by examiner

Primary Examiner—James O. Wilson
Assistant Examiner—Michael C. Henry
(74) Attorney, Agent, or Firm—Anderson Kill & Olick, PC

(57) ABSTRACT

A 2'-deoxyuridine derivative of formula I is bioavailable and thermally stable and forms a gel in water at a low concentration; and, can be employed as a drug delivery vehicle:

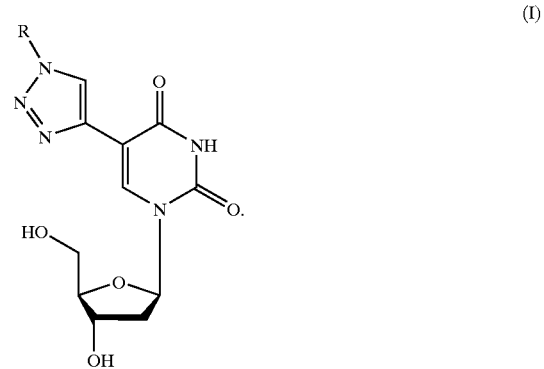

(I)

9 Claims, 5 Drawing Sheets

2'-DEOXYURIDINE DERIVATIVES AND HYDROGELS FORMED THEREWITH

FIELD OF THE INVENTION

The present invention relates to novel 2'-deoxyuridine derivatives which can be used to form hydrogels having a good thermal stability and bioavailability.

BACKGROUND OF THE INVENTION

Various gels having a three-dimensional network have been designed and developed to meet specific physicochemical properties, particularly in terms of reversible volume change in response to stimuli, e.g., pH, temperature and light, so that they can be applied in various fields such as drug delivery, shape memory element and chemical sensor (Kataoka, K., et al., *J. Am. Chem. Soc.,* 1998, 120, 12694; Miyata, T., et al., *Nature,* 1999, 399, 766; Hu, Z., et al, *Science,* 1995, 269, 525; and Holtz, J. H., et al., *Nature,* 1997, 389, 829).

For example, a hydrogel comprised of poly-(N-isopropylacrylamide) substituted with a phenyl boronic group as its backbone changes its volume depending on the concentration of glucose (Kataoka, et al., *J. Am. Chem. Soc.,* 1998, 120, 12694). Further, a hydrogel which changes its volume on contact with an antigen is used as a drug delivery vehicle (Miyata T. et al, *Mature,* 1999, 399, 766).

However, most of the conventional hydrogels are based on high molecular weight polymers which are not satisfactory in terms of drug delivery because of their limited bioavailability.

SUMMARY OF THE INVENTION

Accordingly, it is a primary object of the present invention to provide a novel 2'-deoxyuridine derivative having a low molecular weight, which is capable of forming a hydrogel having a good thermal stability suitable for use as a drug delivery vehicle.

It is another object of the present invention to provide a method for preparing the 2'-deoxyuridine derivative.

It is a further object of the present invention to provide a hydrogel formed with the 2'-deoxyuridine derivative.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1A:
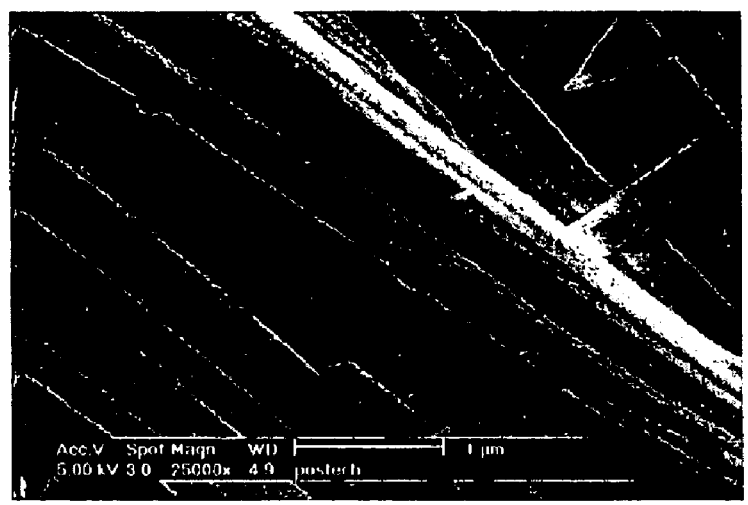
FIGS. 1a to 1d: scanning electron microscopy (SEM) images of hydrogels formed with 1 wt % of 2'-deoxy-5-[1-(phenylmethyl)-1H-1,2,3-triazol-4-yl]-uridine, 2'-deoxy-5-[1-((p-methylphenyl)methyl)-1H-1,2,3-triazol-4-yl]-uridine, 2'-deoxy-5-[1-((p-ethylphenyl)methyl)-1H-1,2,3-triazol-4-yl]-uridine and 2'-deoxy-5-[1-((p-butylphenyl)methyl)-1H-1,2,3-triazol-4-yl]-uridine, respectively.
Figure 1B:
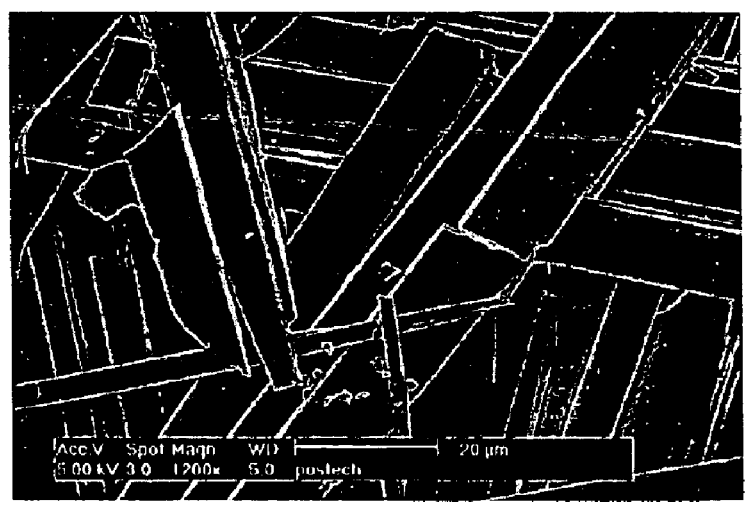
Figure 1C:
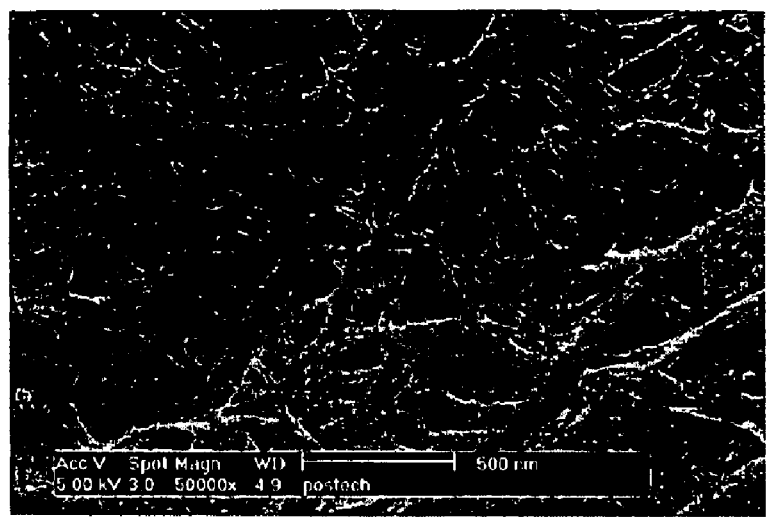
Figure 1D:
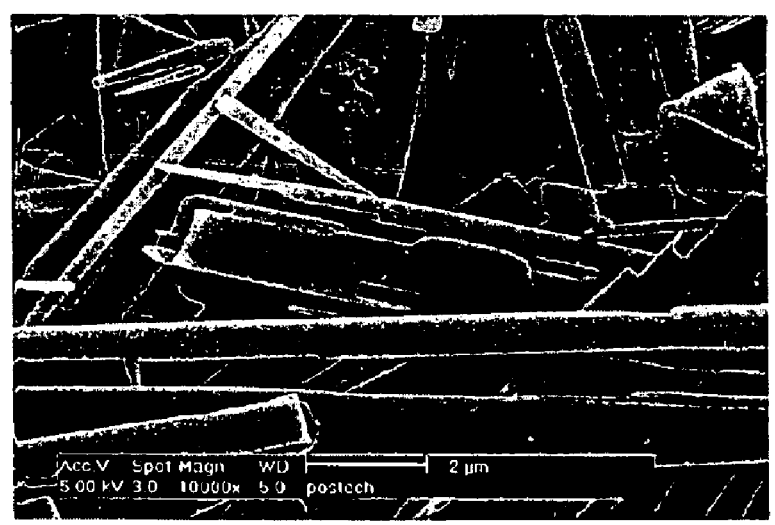
Figure 2A:
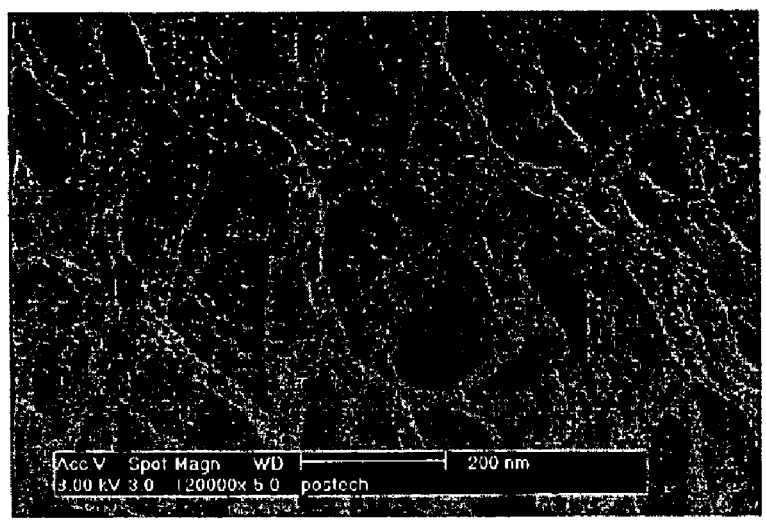
FIGS. 2a to 2d: SEM images of hydrogels formed with 2, 1, 0.5 and 0.25 wt % of 2'-deoxy-5-[1-((p-ethylphenyl)methyl)-1H-1,2,3-triazol-4-yl]-uridine, respectively.
Figure 2B:
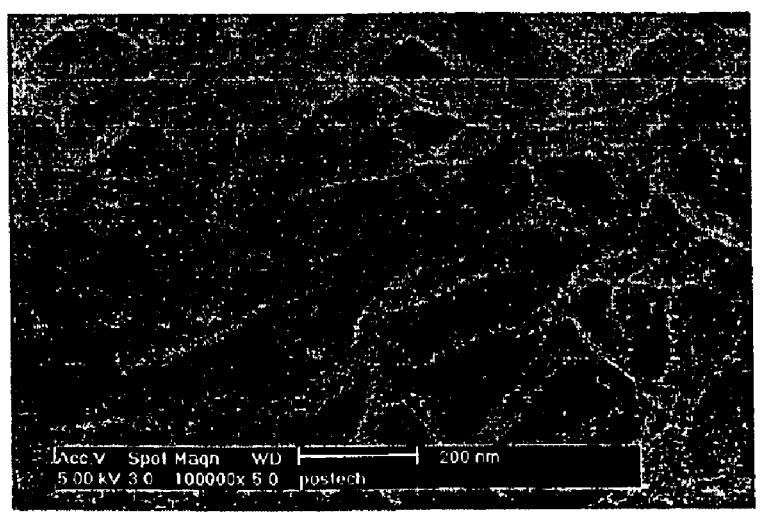
Figure 2C:
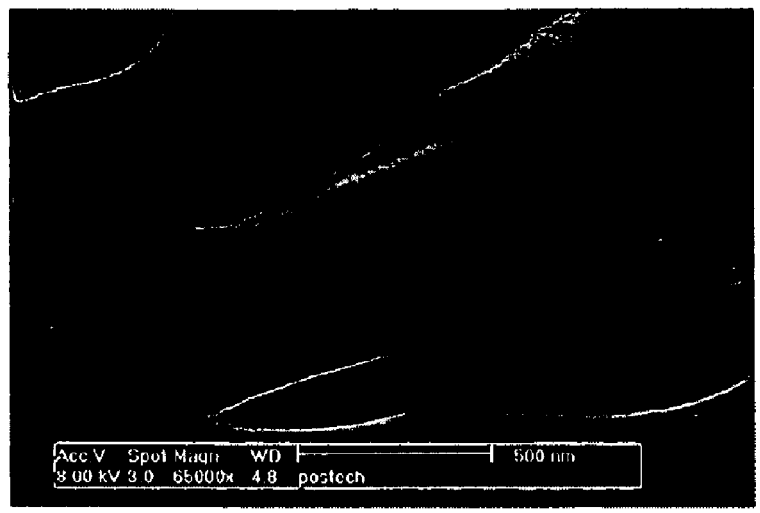
Figure 2D:
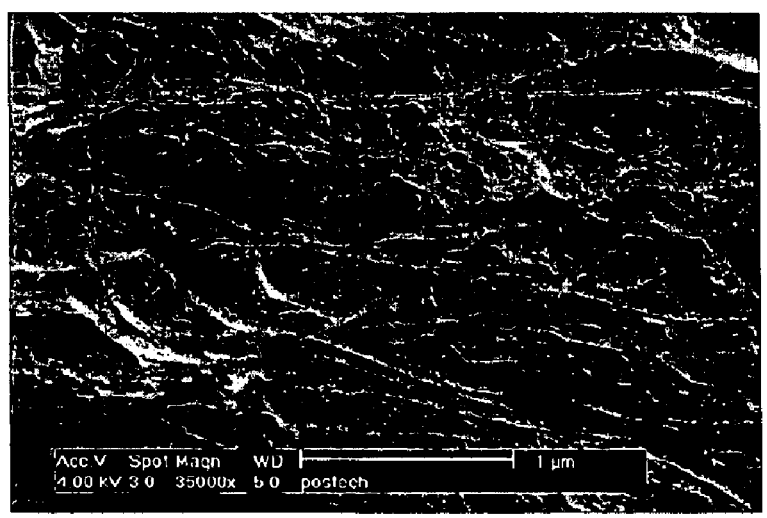

The present invention relates to a 2'-deoxyuridine derivative of formula I:

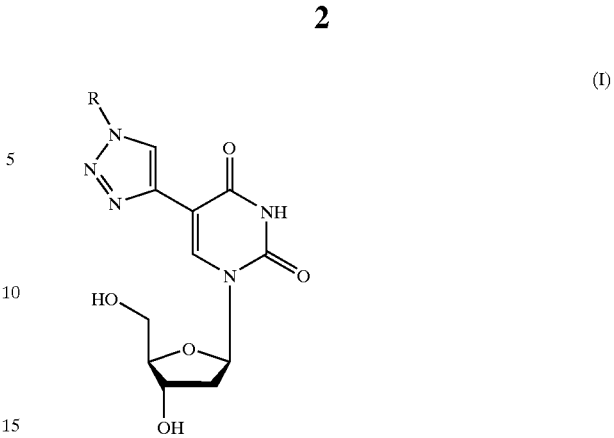

wherein R is benzyl or substituted benzyl.

Preferably, R is benzyl or benzyl having a $C_{1-6}$ alkyl substituent; and more preferably, o-methylbenzyl, m-methylbenzyl, p-methylbenzyl, o-ethylbenzyl, p-ethylbenzyl or p-butylbenzyl.

Preferably, the 2'-deoxyuridine derivative of the present invention is 2'-deoxy-5-[1-(phenylmethyl)-1H-1,2,3-triazole-4-yl]-uridine, 2'-deoxy-5-[1-((methylphenyl)methyl)-1H-1,2,3-triazole-4-yl]-uridine, 2'-deoxy-5-[1-((ethylphenyl)methyl)-1H-1,2,3-triazole-4-yl]-uridine, 2'-deoxy-5-[1-((propylphenyl)methyl)-1H-1,2,3-triazole-4-yl]-uridine, 2'-deoxy-5-[-((butylphenyl)methyl)-1H-1,2,3-triazole-4-yl]-uridine, 2'-deoxy-5-[1-((pentylphenyl)methyl)-1H-1,2,3-triazole-4-yl]-uridine or 2'-deoxy-5-[1-((heptylphenyl)methyl)-1H-1,2,3-triazole-4-yl]-uridine; more preferably, 2'-deoxy-5-[1-(phenylmethyl)-1H-1,2,3-triazole-4-yl]-uridine, 2'-deoxy-5-[1-((o-methylphenyl)methyl)-1H-1,2,3-triazole-4-yl]-uridine, 2'-deoxy-5-[1-((o-methylphenyl)methyl)-1H-1,2,3-triazole-4-yl]-uridine, 2'-deoxy-5-[1-((p-methylphenyl)methyl)-1H-1,2,3-triazole-yl]-uridine, 2'-deoxy-5-[1-((o-ethylphenyl)methyl)-1H-1,2,3-triazole-4-yl]-uridine, 2'-deoxy-5-[1-((p-ethylphenyl)methyl)-1H-1,2,3-triazole-4-yl]-uridine or 2'-deoxy-5-[1-((p-butylphenyl)methyl)-1H-1,2,3-triazole-4-yl]-uridine; and, most preferably, 2'-deoxy-5-[1-((p-methylphenyl)methyl)-1H-1,2,3-triazole-4-yl]-uridine.

The present invention further relates to a method for preparing the above 2'-deoxyuridine derivative. The method comprises the steps of: 1) introducing an acetylene group at the 5-position of 2'-deoxyuridine; and 2) reacting said 2'-deoxyuridine having the acetylene group at the 5-position obtained in step 1) with a benzyl azide derivative.

Prior to step 1) of the inventive method, bromine (Br) or iodine (I), preferably iodine, may be introduced at the 5-position of 2'-deoxyuridine. To introduce iodine, 2'-deoxyuridine may be reacted with triethylamine/iodine chloride, sodium azide ($NaN_3$)/iodine chloride/acetonitrile, or $I_2$ in pyridine in the presence of $PPH_3$. Likewise, to introduce bromine (Br), 2'-deoxyuridine may be reacted with $Br_2/DMF/CCl_4$ or bromosuccinimide/DMF.

In step 1) of the inventive method, an acetylene group may be introduced to replace the Br or I substituent at the 5-position of 2'-deoxyuridine. The acetylene group is preferably protected with a protecting group, e.g., trimethylsilyl, and the introduction of the acetylene group may be performed in the presence of a Pd or Cu catalyst, preferably $(PPh_3)_2PdCl_2$ or CuI.

In step 2) of the inventive method, 2'-deoxyuridine having the acetylene group at the 5-position obtained in step 1) is reacted with a benzyl azide derivative to form a triazole ring at the 5-position thereof. The benzyl azide derivative is preferably benzyl azide or $C_1$-6 alkylbenzyl azide; more preferably, benzyl azide, o-methylbenzyl azide, m-methylbenzyl azide, p-methylbenzyl azide, o-ethylbenzyl azide, p-ethylbenzyl azide or p-butylbenzyl azide; and, most preferably, p-ethylbenzyl azide.

The reaction of step 2) may be performed in the presence of a sodium, lithium or magnesium salt of an alkyne at a low temperature (Akimova, G. S., et al., Zh. Org. Khim., 4, 389–394, 1968). Alternatively, the reaction of step 2) may be performed according to the cycle addition method of sharpless (V. V. Rostovtsev, et al., J. Am. Chem. Soc., 41, 2596, 2002) using tert-butanol/water as the solvent in the presence of $CuSO_4 \cdot 5H_2O$/sodium ascorbate catalyst.

The present invention also relates to a hydrogel formed with the 2'-deoxyuridine derivative of the present invention. The hydrogel is formed by completely dissolving the 2'-deoxyuridine derivative in water by sonication and heating, followed by cooling.

In Example 2 of the present invention, it was observed that the 2'-deoxyuridine derivative of the present invention can form a hydrogel in water at a concentration of only 0.2 wt %.

In Example 4 of the present invention, it has been revealed that the melting point of the 2'-deoxyuridine derivative of the present invention in the gel phase is similar to that in the solid phase. Accordingly, the hydrogel of the 2'-deoxyuridine derivative of the present invention has a good thermal stability.

The following Examples are intended to further illustrate the present invention without limiting its scope.

EXAMPLE 1

Preparation of 2'-deoxyuridine Derivatives 1-1) Preparation of 2'-deoxy-5-iodo-5'-O-(4-methoxytrityl)-uridine 2 g of 5-iodo-2'-deoxyuridine (5.65 mmole) was dissolved in 30 ml of pyridine, 5 ml of TEA and 2.16 g of MMTr-Cl (6.99 mmole) were sequentially added thereto, and stirred at room temperature for 4 hours. Then, pyridine was removed under a reduced pressure with a rotary evaporator, the residue was treated with a mixture of water and $CH_2Cl_2$, the $CH_2Cl_2$ layer was separated, dried under $MgSO_4$, and then, $CH_2Cl_2$ was removed under a reduced pressure. The resulting residue was subjected to column chromatography (silica gel 60, 230–400 meshes, Merck) to obtain the title compound as a pale yellow solid. The chromatography was conducted using a mixture of $CH_2Cl_2$ and methanol as an eluting solution whose mix ratio was gradually changed from 100:1 to 50:1 (v/v).

Yield: 2.89 g (82%);
Melting point: 131.5–132.7° C.;
$^1$H NMR (300 MHz, Acetone-$d_6$) δ 8.13(s, 1H), 7.50–7.53 (m; Ar—H), 7.32–7.47(m; Ar—H), 7.23–7.27(m; Ar—H), 6.92(d, J=8.9 Hz; Ar—H), 6.27(t, J=6.8 Hz, 1H; C1), 4.06–4.09(m, 1H; C3), 3.80(s, 3H; —OCH$_3$), 3.35–3.38(m, 1H; C4), 2.36–2.40(m, 2H; C2), 3.32–3.41(m, 2H; C5);
$^{13}$C NMR (75 MHz, Acetone-$d_6$) δ 160.8, 160.0, 151.0, 150.7, 145.5, 145.4, 136.8, 136.3, 131.4, 129.4, 128.9, 127.9, 124.7, 114.2, 87.8, 87.6, 86.4, 72.5, 68.9, 64.9, 55.7, 55.0, 41.7;
IR (KBr, cm$^{-1}$): 3446, 3060, 2933, 2871, 2835, 1680, 1609, 1509, 1491, 1445, 1299, 1271, 1251, 1181, 1147;
MS(EI$^+$, m/z) 626.07(M$^+$).

1-2) Preparation of 2'-deoxy-5-[(trimethylsilyl)ethynyl]-5'-O-(4-methoxytrityl)-uridine 2 g of 2'-deoxy-5-iodo-5'-O-(4-methoxytrityl)-uridine (3.19 mmole) prepared in 1-1) together with $(PPh_3)_2PdCl_2$ (0.1 eq) and 61 mg of CuI (0.1 eq), were dried under a vacuum, TEA and THF in a ratio of 3:1 were added thereto, and the mixture was purged several times with argon. 0.59 ml of TMS-acetylene (1.3 eq) was then added to the mixture at a temperature ranging from 45 to 50° C., until it became black. The resulting mixture was heated for additional 3 hours to terminate the reaction, and subjected to column chromatography (silica gel 60, 230~400 meshes, Merck) to obtain the title compound as a pale yellow solid. The chromatography was conducted using a mixture of hexane and ethyl acetate as an elution solution whose mix ratio was gradually varied from 3:1 to 1:1 (v/v).

Yield: 1.42 g (75%);
Melting point: 107.2–108.7° C.;
$^1$H NMR (300 MHz, chloroform-$d_6$) δ 8.00(s, 1H), 7.45–7.20(m; Ar—H), 6.85(d, J=8.8 Hz; Ar—H), 6.26(t, J=6.7 Hz, 1H; C1), 4.43–4.45(m, 1H; C3), 3.79(s, 3H; —OCH$_3$), 4.05–4.08(m, 1H, C4), 3.29–3.45(m, 2H; C5), 2.17–2.26(m, 2H; C2), 0.00(s, 9H; -TMS);
$^{13}$C NMR (75 MHz, chloroform-$d_6$) δ 161.7, 158.9, 149.6, 144.2, 142.8, 135.3, 130.5, 128.5, 128.2, 127.3, 113.6, 100.8, 99.9, 95.1, 87.4, 86.8, 86.1, 72.5, 63.8, 60.6, 55.4, 41.5, 21.1, 14.3, –0.2;
IR (KBr, cm$^{-1}$) 3439, 3061, 2956, 2836, 2357, 2162, 1695, 1615, 1558, 1509, 1490, 1278, 1250, 1180, 1091, 1057, 1034;
MS(FAB$^+$, m/z) 618.9(M$_+$+Na).

1-3) Preparation of 2'-deoxy-5-ethynyl-5'-O-(4-methoxytrityl)-uridine 1.40 g of 2'-deoxy-5-[(trimethylsilyl)ethynyl]-5'-O-(4-methoxytrityl)-uridine (2.35 mmole) prepared in 1-2) was dissolved in 20 ml of THF, and then 0.95 ml TBAF (1.4 eq) was added thereto. After 7 hours, the reaction was terminated, THF was removed using a rotary evaporator, and the resulting residue was subjected to column chromatography (silica gel 60, 230–400 meshes, Merck) to obtain the title compound as a solid. The chromatography was conducted using a mixture of $CH_2Cl_2$ and methanol as an eluting solution whose mix ratio was gradually varied from 100:1 to 50:1 (v/v).

Yield: 1.26 g (QUANT.);
Melting point: 127.8–129.3° C.;
$^1$H NMR (300 MHz, chloroform-$d_6$) δ 8.34(s, 1H), 8.08(s, 1H), 7.22–7.46(m; Ar—H), 6.85–6.88(m; Ar—H), 6.29(t, J=6.5 Hz, 1H; C1), 4.57(m, 1H; C3), 4.09(m, 1H; C4), 3.81(m, 3H; —OCH$_3$), 3.37–3.45(m, 2H; C5), 2.90(s, 1H; —CCH), 2.25–2.56(m, 2H; C2);
$^{13}$C NMR (75 MHz, chloroform-$d_6$) δ 161.8, 159.0, 149.5, 144.2, 143.8, 135.2, 130.6, 128.5, 128.2, 127.4, 113.6, 99.5, 87.6, 86.8, 86.1, 82.2, 74.4, 72.4, 63.8, 55.5, 53.6, 41.6;
IR (KBr, cm$^{-1}$) 3445, 3285, 3061, 2932, 2836, 1696, 1623, 1509, 1490, 1462, 1278, 1251, 1180, 1089, 1034;
MS(FAB$^+$, m/z) 546.9(M$^+$+Na).

1-4) Preparation of 2'-deoxy-5-[1-(phenylmethyl)-1H-1,2,3-triazol-4-yl]-uridine 1-4-1) Preparation of Benzyl Azide 2.07 ml of benzyl alcohol (20 mmole), 2.99 g of DMAP (1.2 eq) and 1.86 ml of MeSOCl$_2$ (1.2 eq) were sequentially added to 25 ml of DMF. After stirring the mixture for 6 hours, 3.96 g of NaN$_3$ (3 eq) was added thereto, and the mixture was stirred for 12 hours. The reaction mixture was treated with a mixture of diethyl ether and water, the ether extract was dried under MgSO$_4$, ether was removed under a reduced pressure, and the resulting residue was subjected to column chromatography (silica gel 60, 230~400 meshes, Merck) to obtain the title compound as a pale yellow liquid.

The chromatography was conducted using a mixture of hexane and $CH_2Cl_2$ as an eluting solution whose mix ratio was gradually varied from 2:1 to 1:1 (v/v).

Yield: 2.61 g (QUANT.);

$^1$H NMR (300 MHz, chloroform-$d_6$) δ 7.27–7.40(m, 5H; Ar—H), 4.29(s, 2H; —$CH_2$—);

$^{13}$C NMR (75 MHz, chloroform-$d_6$) δ 135.5, 128.9, 128.4, 128.3, 54.8;

IR (NaCl, cm$^{-1}$) 3088, 3066, 3032, 2932, 2877, 2097, 1496, 1454, 1365, 1350, 1256, 1201, 1160;

MS (EI$^+$, m/z) 133.08(M$^+$).

1-4-2) Preparation of 2'-deoxy-5-[1-(phenylmethyl)-1H-1,2,3-triazol-4-yl]-5'-O-(4-methoxytrityl)-uridine 380 mg of the compound (0.72 mmole) obtained in 1-3) was dissolved in 7 ml of tert-BuOH:$H_2O$ (1:1(v/v)), and then, 18 mg of sodium ascorbate, 2 mg of cooper sulfate pentahydrate and 288 mg of benzyl azide were added thereto. After the mixture was stirred for 4 days, the solvent (tert-BuOH:$H_2O$) was evaporated under a reduced pressure using a rotary evaporator. The resulting residue was subjected to column chromatography (silica gel 60, 230–400 meshes, Merck) to obtain the title compound as a pale yellow solid. The chromatography was conducted using a mixture of hexane and ethyl acetate as an eluting solution whose mix ratio was gradually varied from 1:1 to 1:2(v/v).

Yield: 415 mg (81%);

Melting point: 181.7–183.2° C.;

$^1$H NMR (300 MHz, chloroform-$d_6$) δ 8.83(s, 1H), 8.41(s, 1H), 7.15–7.45(m; Ar—H), 6.80–6.84(m; Ar—H), 6.26(t, J=6.7 Hz, 1H; C1), 5.48(s, 2H; —$CH_2$—), 4.37(m, 1H; C3), 4.00–4.01(m, 1H; C4), 3.73(s, 3H; —$OCH_3$), 3.36–3.51(m, 2H; C5), 2.39(m, 2H; C2);

$^{13}$C NMR (75 MHz, acetone-$d_6$) δ 159.6, 159.5, 149.1, 145.6, 140.9, 136.4, 131.2, 130.1, 129.7, 129.3, 128.9, 128.6, 128.4, 127.8, 127.6, 113.9, 113.7, 89.0, 87.4, 86.4, 81.8, 55.5, 55.0, 54.2, 52.1, 49.8;

IR (KBr, cm$^{-1}$) 3456, 3056, 2933, 1696, 1609, 1540, 1509, 1447 1296, 1250, 1180, 1097, 1033;

MS(FAB$^+$, m/z) (M$^+$+Na).

1-4-3) Preparation of 2'-deoxy-5-[1-(phenylmethyl)-1H-1,2,3-triazol-4-yl]-uridine 415 mg of the compound (0.63 mmole) obtained in 1-4-2) was dissolved in 50 ml of 80% acetic acid in $CH_2Cl_2$, stirred at 90° C. for 4 hours, and the solvent (acetic acid in $CH_2Cl_2$) was removed under a reduced pressure. The resulting residue was subjected to column chromatography (silica gel 60, 230–400 meshes, Merck), and to recrystallization from methanol and water, to obtain the title compound as a solid. The chromatography was conducted using a mixture of $CH_2Cl_2$ and methanol as an eluting solution whose mix ratio was gradually varied from 100:1 to 10:1 (v/v).

Yield: 206 mg (83%);

Melting point: 200.5° C.;

$^1$H NMR (300 MHz, MeOD) δ 8.59(s, 1H; H6), 8.27(s, 1H), 7.33(br, 5H; Ar—H), 6.31(t, J=6.8 Hz, 1H; C1), 5.59(s, 2H; $CH_2$), 4.41(br, 1H; C3), 3.93(m, 1H; C4), 3.84–3.71(m, 2H; C5), 2.27(m, 2H; C2);

$^3$C NMR (75 MHz, Acetone-$d_6$) δ 153.2, 146.5, 137.3, 129.8, 129.2, 129.0, 123.0, 89.0, 86.4, 72.6, 63.0, 54.2, 41.4, 19.5, 14.8;

IR (ZnSe, cm$^{-1}$); 3232, 1714, 1680, 1541, 1475, 1450, 1425, 1279, 1227, 1103;

HRMS calcd for $C_{19}H_{21}N_5O_5$: 385.139. Found: 385.138 (M$^+$+H) 133.2.

1-5) Preparation of 2'-deoxy-5-[1-((o-methylphenyl)methyl)-1H-1,2,3-triazol-4-yl]-uridine 1-5-1) Preparation of o-methybenzyl Azide The title compound was obtained as a pale yellow liquid by repeating the procedure of 1-4-1), except for employing 2.44 ml of o-methylbenzyl alcohol (20 mmole) instead of benzyl alcohol.

Yield: 3.26 g (QUANT.);

$^1$H NMR (300 MHz, chloroform-$d_6$) δ 7.15–7.26(m, 4H; Ar—H), 4.30(s, 2H; —$CH_2$—), 2.33(s, 3H; —$CH_3$);

$^{13}$C NMR (75 MHz, chloroform-$d_6$) δ 136.9, 133.5, 130.8, 129.4, 128.7, 126.3, 53.1, 19.1;

IR (NaCl, cm$^{-1}$) 3023, 2932, 2883, 2097, 1719, 1605, 1493, 1460, 1381, 1343, 1248, 1219, 1180, 1115; MS (EI$^+$, m/z) 147.16(M$^+$).

1-5-2) Preparation of 2'-deoxy-5-[1-((o-methylphenyl)methyl)-1H-1,2,3-triazol-4-yl]-5'-O-(4-methoxytrityl)-uridine The title compound was obtained as a pale yellow solid by repeating the procedure of 1-4-2), except for employing o-methylbenzyl azide instead of benzyl azide.

Yield: 208 mg (66%);

Melting point: 186.1–187.9° C.;

$^1$H NMR (300 MHz, chloroform-$d_6$) δ 9.99(s, 1H), 8.35(s, 1H), 7.96(s, 1H), 6.99–7.30(m; Ar—H), 6.69(br; Ar—H), 6.21(br, 1H; Cl), 5.34(s, 2H; —$CH_2$—), 4.30(br, 1H; C3), 4.00–4.03(m, 1H; C4), 3.58–3.60(m, 3H; —$OCH_3$), 3.29–3.34(m, 2H; C5), 2.15(br, 2H; C2), 1.93–1.95(m, 3H; $CH_3$);

$^{13}$C NMR (75 MHz, chloroform-$d_6$) δ 161.5, 158.7, 150.0, 144.3, 139.2, 136.7, 136.3, 135.3, 132.8, 131.0, 130.5, 129.2, 129.1, 128.4, 128.0, 127.0, 126.7, 122.4, 106.4, 87.1, 86.2, 72.4, 64.0, 60.8, 55.3, 52.3, 21.2, 14.3;

IR (KBr, cm$^{-1}$) 3420, 3057, 2925, 1690, 1547, 1509, 1448, 1353, 1252, 1181, 1042;

MS(FAB$^+$, m/z) (M$^+$+Na).

1-5-3) Preparation of 2'-deoxy-5-[1-((o-methylphenyl)methyl)-1H-1,2,3-triazol-4-yl]-uridine The title compound was obtained as a solid by repeating the procedure of 1-4-3), except for employing the compound obtained in 1-5-2) instead of the compound obtained in 1-4-2).

Yield: 206 mg (56%);

Melting point: 167.8–170.2° C.;

$^1$H NMR (300 MHz, Acetone-$d_6$) δ 8.57(s, 1H; NH), 8.18(s, 1H; triazole-H), 7.19–7.27(m, 4H; Ar—H), 6.42(t, J=6.8 Hz, 1H; C1), 5.69(s, 2H; —$CH_2$—), 4.53(br, 1H; C3), 4.25–4.36(m, 2H; C5), 4.17–4.20(m, 1H; C4), 2.38–2.41(m, 2H; C2), 2.19(s, 3H; $CH_3$);

$^{13}$C NMR (75 MHz, DMSO-$d_6$) δ 161.1, 149.6, 138.5, 135.9, 134.1, 129.6, 128.2, 122.3, 105.1, 87.6, 84.7, 70.6, 61.4, 50.9, 41.0, 38.7, 18.5;

IR (KBr, cm$^{-1}$) 3439, 3061, 2956, 2162, 1695, 1615, 1509, 1448, 1278, 1250, 1180, 1091;

HRMS calcd for $C_{19}H_{21}N_5O_5$: 399.154. Found: 399.154 (M$^+$+H).

1-6) Preparation of 2'-deoxy-5-[1-((m-methylphenyl)methyl)-1H-1,2,3-triazol-4-yl]-uridine 1-6-1) Preparation of m-methybenzyl Azide The title compound was obtained as a pale yellow liquid by repeating the procedure of 1-4-1), except for employing 2.45 ml of m-methylbenzyl alcohol (20 mmole) instead of benzyl alcohol.

Yield; 3.01 g (QUANT.);

$^1$H NMR (300 MHz, chloroform-$d_6$) δ 7.08–7.27(m, 4H; Ar—H), 4.26(s, 2H; —$CH_2$—), 2.35(s, 3H; —$CH_3$);

$^{13}$C NMR (75 MHz, chloroform-$d_6$) δ 138.7, 135.4, 129.2, 129.1, 128.8, 125.4, 54.9, 21.5;

IR (NaCl, cm⁻¹) 3026, 2923, 2874, 2099, 1611, 1592, 1490, 1454, 1379, 1342, 1265, 1237, 1158, 1094;

MS(EI⁺, m/z) 147.09(M⁺).

1-6-2) Preparation of 2'-deoxy-5-[1-((m-methylphenyl)methyl)-1H-1,2,3-triazol-4-yl]-5'-O-(4-methoxytrityl)-uridine The title compound (yiled: 226 mg (72%)) was obtained as a pale yellow solid by repeating the procedure of 1-4-2), except for employing m-methylbenzyl azide instead of benzyl azide.

1-6-3) Preparation of 2'-deoxy-5-[1-((m-methylphenyl)methyl)-1H-1,2,3-triazol-4-yl]-uridine The title compound was obtained as a solid by repeating the procedure of 1-4-3), except for employing the compound obtained in 1-6-2) instead of the compound obtained in 1-4-2).

Yield: 206 mg (56%);

Melting point: 131.5–132.7° C.;

¹H NMR (300 MHz, Acetone-d₆) δ 8.57(s, 1H; NH), 8.28(s, 1H; triazole-H), 7.14–7.29(m, 4H; Ar—H), 6.42(t, J=6.8 Hz, 1H; C1), 5.62(s, 2H; —CH₂—), 4.54(br, 1H; C3), 4.25–4.36(m, 2H; C5), 4.17–4.20(m, 1H; C4), 2.36–2.41(m, 2H; C2), 2.19(s, 3H; CH₃);

IR (KBr, cm⁻¹): 3421, 3240, 3164, 3079, 2954, 1688, 1553, 1476, 1457, 1440, 1383, 1362, 1282, 1249, 1231, 1199, 1091, 1064, 1046, 1000;

HRMS-EI (m/z): [M+H]⁺ calcd for C₁₉H₂₁N₅O₅, 399.154; found, 399.154.

1-7) Preparation of 2'-deoxy-5-[1-((p-methylphenyl)methyl)-1H-1,2,3-triazol-4-yl]-uridine 1-7-1) Preparation of p-methylbenzyl Azide The title compound was obtained as a pale yellow liquid by repeating the procedure of 1-4-1), except for employing 2.07 ml of p-methylbenzyl alcohol (20 mmole) instead of benzyl alcohol.

Yield: 3.40 g (QUANT.);

¹H NMR (300 MHz, chloroform-d₆) δ 7.15–7.21(m, 4H; Ar—H), 4.25(s, 2H; —CH₂—), 2.34(s, 3H; —CH₃);

¹³C NMR (75 MHz, chloroform-d₆) δ 138.2, 132.5, 129.6, 128.4, 54.8, 21.2;

IR (NaCl, cm⁻¹) 2924, 2878, 2097, 1615, 1515, 1449, 1345, 1254;

MS(EI⁺, m/z) 147.14(M⁺).

1-7-2) Preparation of 2'-deoxy-5-[1-((p-methylphenyl)methyl)-1H-1,2,3-triazol-4-yl]-5'-O-(4-methoxytrityl)-uridine The title compound was obtained as a pale yellow solid by repeating the procedure of 1-4-2), except for employing p-methylbenzyl azide instead of benzyl azide.

Yield: 240 mg (76%);

Melting point: 186.9–188.4° C.;

¹H NMR (300 MHz, chloroform-d₆) δ 8.44(s, 1H), 8.16(s, 1H), 7.09–7.42(m; Ar—H), 6.76–6.78(m; Ar—H), 6.32(t, J=6.5 Hz, 1H; C1), 5.38(s, 2H; —CH₂—), 4.42(m, 1H; C3), 4.03–4.11(m, 1H; C4), 3.65–3.71(m, 3H; —OCH₃), 3.65–3.71(m, 2H; C5), 2.27–2.45(m, 5H; C2+CH₃);

¹³C NMR (75 MHz, chloroform-d₆) δ 161.6, 158.7, 150.0, 144.4, 139.3, 138.5, 136.3, 135.4, 132.0, 130.5, 129.7, 128.5, 128.1, 128.0, 127.2, 122.4, 106.4, 87.1, 86.2, 86.0, 72.3, 64.1, 60.5, 55.2, 53.9, 21.2, 14.3;

IR (KBr, cm⁻¹) 3420, 3057, 2925, 1690, 1547, 1509, 1448, 1353, 1252, 1181, 1042;

MS(FAB⁺, m/z) (M⁺+Na).

1-7-3) Preparation of 2'-deoxy-S[1-((p-methylphenyl)methyl)-1H-1,2,3-triazol-4-yl]-uridine The title compound was obtained as a solid by repeating the procedure of 1-4-3), except for employing the compound obtained in 1-7-2) instead of the compound obtained in 1-4-2).

Yield: 206 mg (56%);

Melting point: 226° C.;

¹H NMR (300 MHz, Acetone-d₆) δ 8.56(s, 1H; NH), 8.26(s, 1H; triazole-H), 7.28(d, J=8.1 Hz, 2H; Ar—H), 7.20(d, J=8.0 Hz, 2H; Ar—H), 6.42(t, J=6.8 Hz, 1H; C1), 5.62(s, 2H; —CH₂—), 4.55(br, 1H; C3), 4.25–4.36(m, 2H; C5), 4.17(m, 1H; C4), 2.36–2.40(m, 2H; C2), 2.31(s, 3H; CH₃);

¹³C NMR (75 MHz, DMSO-d₆) δ 161.4, 149.9, 139.3, 137.7, 136.4, 133.4, 129.5, 128.2, 122.6, 105.5, 87.9, 85.0, 70.9, 61.7, 52.5, 40.6, 39.0, 21.0;

IR (ZnSe, cm⁻¹): 3367, 3257, 3161, 2928, 1734, 1716, 1688, 1551, 1454, 1358, 1283, 1230, 1198, 1149, 1078;

HRMS calcd for C₁₉H₂₁N₅O₅: 399.154. Found: 399.154 (M⁺+H).

1-8) Preparation of 2'-deoxy-5-[1-((o-ethylphenyl)methyl)-1H-1,2,3-triazol-4-yl]-uridine 1-8-1) Preparation of o-ethylbenzyl Azide The title compound was obtained as a pale yellow liquid by repeating the procedure of 1-4-1), except for employing 2.75 ml of o-ethylbenzyl alcohol (20 mmole) instead of benzyl alcohol.

Yield: 2.75 g (QUANT.);

¹H NMR (300 MHz, chloroform-d₆) δ 7.19–7.34(m, 4H; Ar—H), 4.37(s, 2H; —CH₂—), 2.71 (q, J=7.6 Hz, 2H; —CH₂CH₃), 1.23–1.29(m, 3H; —CH₃);

¹³C NMR (75 MHz, chloroform-d₆) δ 143.0, 133.0, 129.9, 129.2, 129.1, 126.4, 52.8, 25.6, 14.4;

IR (NaCl, cm⁻¹) 3067, 3022, 2969, 2935, 2877, 2098, 1699, 1605, 1558, 1491, 1456, 1344, 1251, 1170;

MS(EI⁺, m/z) 161.15(M⁺).

1-8-2) Preparation of 2'-deoxy-5-[1-((o-ethylphenyl)methyl)-1H-1,2,3-triazol-4-yl]-5'-O-(4-methoxytrityl)-uridine The title compound (yield: 223 mg (71%)) was obtained as a pale yellow solid by repeating the procedure of 1-4-2), except for employing o-ethylbenzyl azide instead of benzyl azide.

1-8-3) Preparation of 2'-deoxy-5-[1-((o-ethylphenyl)methyl)-1H-1,2,3-triazol-4-yl]-uridine The title compound was obtained as a solid by repeating the procedure of 1-4-3), except for employing the compound obtained in 1-8-2) instead of the compound obtained in 1-4-2).

Yield: 166 g (87%);

Melting point: 169.2–172.5° C.;

¹H NMR (300 MHz, Acetone-d₆) δ 8.84(s, 1H; H6), 8.18(s, 1H; triazole-H), 7.28–7.35(m, 2H; Ar—H), 7.19–7.23(m, 2H; Ar—H), 6.39(t, J=6.9 Hz, 1H; C1), 5.71(s, 2H; —CH₂—), 4.27–4.30(m, 1H; C3), 4.01–4.03(m, 1H; C4), 3.81–3.89(m, 2H; C5), 2.33–2.37(m, 2H; C2), 1.14–1.19(m, 3H; —CH₃);

¹³C NMR (75 MHz, Acetone-d₆) δ 161.9, 150.6, 143.5, 140.6, 137.3, 130.3, 129.9, 129.7, 127.3, 122.9, 106.6, 89.0, 86.4, 72.5, 63.0, 51.9, 41.4, 25.9, 15.5;

IR (NaCl, cm⁻¹): 3446, 2934, 1696, 1643, 1542, 1472, 1445, 1343, 1270, 1201, 1097, 1056.

1-9) Preparation of 2'-deoxy-5-[1-((p-ethylphenyl)methyl)-1H-1,2,3-triazol-4-yl]-uridine 1-9-1) Preparation of p-ethylbenzyl Azide The title compound was obtained as a pale yellow liquid by repeating the procedure of 1-4-1), except for employing 2.70 ml of p-ethylbenzyl alcohol (20 mmole) instead of benzyl alcohol.

Yield: 2.78(QUANT.);

¹H NMR (300 MHz, chloroform-d₆) δ 7.20(s, 4H; Ar—H), 4.25(s, 2H; —CH₂—), 2.60–2.67(m, 2H; —CH₂CH₃), 1.20–1.25(m, 3H; —CH₃);

$^{13}$C NMR (75 MHz, chloroform-d$_6$) δ 144.5, 132.7, 128.4, 54.7, 28.7, 15.6;
IR (NaCl, cm$^{-1}$) 3052, 3024, 2967, 2932, 2874, 2097, 1614, 1514, 1455, 1420, 1344, 1255, 1206, 1182, 1059;
MS (EI$^+$, m/z) 161.12(M$^+$).

1-9-2) Preparation of 2'-deoxy-5-[1-((p-ethylphenyl)methyl)-1H-1,2,3-triazol-4-yl]-5'-O-(4-methoxytrityl)-uridine The title compound was obtained as a pale yellow solid by repeating the procedure of 1-4-2), except for employing o-ethylbenzyl azide instead of benzyl azide.
Yield: 410 mg (64%);
Melting point: 188.9–190.3° C.;
$^1$H NMR (300 MHz, chloroform-d$_6$) δ 8.41(s, 1H), 8.15(s, 1H), 8.05(s, 1H), 7.41–7.43(m; Ar—H), 7.15–7.34(m; Ar—H), 6.82–6.85(m; Ar—H), 6.28(t, J=6.5 Hz, 1H; C1), 5.48(s, 2H; —CH$_2$—), 4.38–4.42(m, 1H; C3), 4.00–4.01(m, 1H; C4), 3.77(s, 3H; —OCH$_3$), 3.38–3.54(m, 2H; C5), 2.60–2.68(m, 2H; C2), 2.28–2.49(m, 2H; —CH$_2$CH$_3$), 1.22 (m, 3H; CH$_3$);
$^{13}$C NMR (75 MHz, chloroform-d$_6$) δ 161.2, 158.9, 149.7, 145.1, 144.3, 139.4, 136.3, 135.4, 132.2, 130.6, 128.8, 128.6, 128.3, 128.1, 127.2, 122.4, 113.5, 109.7, 106.6, 87.4, 85.9, 72.7, 64.1, 60.6, 55.4, 54.2, 40.4, 29.9, 28.7, 15.6;
IR (KBr, cm$^{-1}$) 3418, 3057, 2927, 1690, 1608, 1547, 1510, 1448, 1353, 1252, 1181, 1042;
MS(FAB$^+$, m/z) (M$^+$+Na).

1-9-3) Preparation of 2'-deoxy-5-[1-((p-ethylphenyl)methyl)-1H-1,2,3-triazol-4-yl]-uridine The title compound was obtained as a solid by repeating the procedure of 1-4-3), except for employing the compound obtained in 1-9-2) instead of the compound obtained in 1-4-2).
Yield: 327 mg (85%);
Melting point: 201° C.;
$^1$H NMR (300 MHz, Acetone-d$_6$) δ 8.61(s, 1H), 8.28(s, 1H), 7.23(m, 2H; Ar—H), 7.12(m, 2H; Ar—H), 6.27(t, J=6.8 Hz, 1H; C1), 5.52(s, 1H; —CH$_2$—), 4.42(br, 1H), 3.94(m, 1H), 3.71(m, 2H), 2.49(m, 2H), 2.30–2.22(m, 2H), 1.07(t, 3H; CH$_3$);
$^{13}$C NMR (75 MHz, Acetone-d$_6$) δ 162.0, 150.6, 145.1, 139.9, 137.1, 133.2, 128.7, 126.3, 123.1, 105.9, 88.0, 86.0, 71.3, 61.8, 53.9, 49.1, 40.4, 28.5, 15.4;
IR (ZnSe, cm$^{-1}$): 3261, 2970, 1738, 1697, 1666, 1543, 1487, 1456, 1097, 1053;
HRMS calcd for C$_{20}$H$_{23}$N$_5$O$_5$: 413.170. Found: 413.170 (M$^+$+H).

1-10) Preparation of 2'-deoxy-5-[1-((p-butylphenyl)methyl)-1H-1,2,3-triazol-4-yl]-uridine 1-10-1) Preparation of p-butylbenzyl Azide The title compound was obtained as a pale yellow liquid by repeating the procedure of 1-4-1), except for employing 3.41 ml of p-butylbenzyl alcohol (20 mmole) instead of benzyl alcohol.
Yield: 3.38 g (89%);
$^1$H NMR (300 MHz, chloroform-d$_6$) δ 7.16–7.22(m, 4H; Ar—H), 4.26(s, 2H; —CH$_2$—), 2.55–2.62(m, 2H; —CH$_2$(CH$_2$)$_2$CH$_3$), 1.57(sex, J=7.6 Hz, 2H; —CH$_2$CH$_2$CH$_3$), 1.34(sex, J=7.4 Hz, 2H; —(CH$_2$)$_2$CH$_2$CH$_3$), 0.87–0.94(m, 3H; —(CH$_2$)$_3$CH$_3$);
$^{13}$C NMR (75 MHz, chloroform-d$_6$) δ 143.2, 132.7, 129.0, 128.4, 54.7, 35.5, 33.7, 22.5, 14.1;
IR (NaCl, cm$^{-1}$) 2957, 2930, 2859, 2097, 1700, 1651, 1558, 1540, 1512, 1457, 1420, 1342, 1251;
MS (EI$^+$, m/z) 189.17(M$^+$).

1-10-2) Preparation of 2'-deoxy-5-[1-((p-butylphenyl)methyl)-1H-1,2,3-triazol-4-yl]-5'-O-(4-methoxytrityl)-uridine The title compound was obtained as a pale yellow solid by repeating the procedure of 1-4-2), except for employing p-butylbenzyl azide instead of benzyl azide.
Yield: 415 mg (81%);
Melting point: 190.5–192.2° C.;
$^1$H NMR (300 MHz, chloroform-d$_6$) δ 10.36(s, 1H; NH), 8.44(s, 1H; triazole-H), 8.17(s, 1H), 7.11–7.41(m; Ar—H), 6.76–6.79(m; Ar—H), 6.32(br, 1H; C1), 5.40(s, 2H; —CH$_2$—), 4.42(br, 1H; C3), 4.09–4.11(m, 2H; C5), 3.92(br, 1H; C4), 3.66(s, 3H; —OCH$_3$), 2.52–2.57(m, 2H; C2), 1.51–1.56(m, 2H; —CH$_2$—C$_3$H$_7$), 1.18–1.34(m, 4H; —CH$_2$-(CH$_2$)$_2$—CH$_3$), 0.86(m, 3H; —C$_3$H$_6$CH$_3$);
$^{13}$C NMR (75 MHz, chloroform-d$_6$) δ 161.7, 158.6, 150.1, 144.3, 139.3, 136.4, 132.1, 130.5, 129.1, 128.4, 128.0, 127.9, 127.0, 122.5, 113.3, 106.3, 87.0, 86.3, 86.0, 72.2, 64.1, 60.7, 55.2, 53.9, 40.4, 35.4, 33.6, 22.4, 21.1, 14.3, 14.0;
IR (ZnSe, cm$^{-1}$): 3377, 3248, 3157, 3059, 2955, 2928, 2852, 2511, 1726, 1695, 1662, 1549, 1466, 1425, 1367, 1259, 1182, 1113, 1074, 1037;
MS(FAB$^+$, m/z) 441.3(M$^+$+H).

1-10-3) Preparation of 2'-deoxy-5-[1-((p-butylphenyl)methyl)-1H-1,2,3-triazol-4-yl]-uridine The title compound was obtained as a solid by repeating the procedure of 1-4-3), except for employing the compound obtained in 1-10-2) instead of the compound obtained in 1-4-2).
Yield: 206 mg (81%);
Melting point: 202° C.;
$^1$H NMR (300 MHz, Acetone-d$_6$) δ 8.56(s, 1H; NH), 8.28(s, 1H; triazole-H), 7.30(d, J=8.1 Hz, 2H; Ar—H), 7.22(d, J=8.0 Hz, 2H; Ar—H), 6.42(t, J=6.8 Hz, 1H; C1), 5.63(s, 2H; —CH$_2$—), 4.54(br, 1H; C3), 4.29–4.35(m, 2H; C5), 4.18(m, 1H; C4), 2.60(t, J=7.7 Hz, 2H; —CH$_2$—C$_3$H$_7$), 2.26–2.40(m, 2H; C2), 1.52–1.62(m, 2H; —(CH$_2$)—CH$_2$—C$_2$H$_5$), 1.33(sex, J=7.4 Hz, 2H; —(CH$_2$)$_2$—CH$_2$—CH$_3$), 0.90(t, J=7.3 Hz, 3H; CH$_3$);
$^{13}$C NMR (75 MHz, Acetone-d$_6$) δ 161.7, 150.3, 140.5, 136.3, 134.4, 129.8, 129.0, 122.9, 106.9, 86.0, 85.8, 72.3, 64.7, 63.4, 54.1, 41.3, 34.5, 23.0, 21.1, 14.2;
IR (ZnSe, cm$^{-1}$): 3377, 3248, 3157, 3059, 2955, 2928, 2852, 2511, 1726, 1695, 1662, 1549, 1466, 1425, 1367, 1259, 1182, 1113, 1074, 1037;
MS(FAB$^+$, m/z) 441.3(M$^+$+H).

EXAMPLE 2

Gelation Test

In order to determine the extent of gelation of the 2'-deoxyuridine derivative of the present invention, the "stable-to-inversion-of-the-container" method was performed (see F. M. Menger and K. L Caran., *J. Am. Chem. Soc.*, 122, 11679, 2000).

Each of 2'-deoxyuridine derivatives prepared in Example 1 was mixed with water in an amount corresponding to a concentration of 2 wt %, completely dissolved by sonication and heating, and then cooled at room temperature for 20 minutes to induce the formation of a gel. Then, the vessel containing the gel was inverted to see whether or not the content poured out. The gel was called "stable" in case that the content did not pour out, and "unstable", when the content poured out.

Further, the minimum concentration at which a gel was formed (hereinafter, minimum gel concentration) was measured for each of the 2'-deoxyuridine derivatives. The results are represented in Table 1.

TABLE 1

| 2'-deoxy derivative prepared in Example 1 | State | Minimum gel concentration (wt %) |
|---|---|---|
| The derivative prepared in 1-4) | White opaque gel | 0.3 |
| The derivative prepared in 1-5) | Unstable white opaque gel | 3 |
| The derivative prepared in 1-6) | Unstable white opaque gel | 1 |
| The derivative prepared in 1-7) | White opaque gel | 0.6 |
| The derivative prepared in 1-8) | Unstable white opaque gel | 2 |
| The derivative prepared in 1-9) | White opaque gel | 0.2 |
| The derivative prepared in 1-10) | White opaque gel | 0.8 |

The above results showed that the 2'-deoxyuridine derivatives prepared in 1-7), 1-9) and 1-10) having alkyl chains in the para position, had good gelation ability. The 2'-deoxyuridine derivative prepared in 1-9), in particular, formed a gel in water at a concentration of only 0.2 wt % o, and therefore, exhibited the best gelation ability among the 2'-deoxyuridine derivatives prepared in Example 1.

EXAMPLE 3

Observation of Inner Structures of Gels Prepared from the 2'-Deoxyuridine Derivatives The aggregation mode of the gel formed with the 2'-deoxyurindine derivative was observed by Scanning Electron Microscopy (SEM). Gels were prepared using the 2'-deoxyuridine derivatives prepared in 1-4), 1-7), 1-9) and 1-10) by the method of Example 2. Each of the gels was heated to obtain a sol, and a small amount of the sol was converted to a gel cake, which was lyophilized under a vacuum at the liquid nitrogen temperature to remove the solvent, coated with platinum, and examined by SEM.

The SEM images showed that the 2'-deoxyuridine derivatives prepared in 1-4), 1-7) and 1-10) formed gels having a lamellar structure, while the 2'-deoxyuridine derivative prepared in 1-9) formed a gel having a fiber structure. The fiber structure can retain more water than the lamellar structure, and therefore, the 2'-deoxyuridine derivative prepared in 1-9) forms a gel at a minimum concentration.

When the concentration of the 2'-deoxyuridine derivative prepared in 1-9) was lowered from 2 to 0.25 wt %, the SEM image of the gel prepared therefrom showed a looser fiber structure having a larger void volume than the gel formed at the higher concentration (see FIG. 2). Thus, the result shows that as the fiber structure becomes looser, more water is retained between the fiber bundles.

EXAMPLE 4

Analysis of Thermal Stability of Hydrogel

Figure 3:
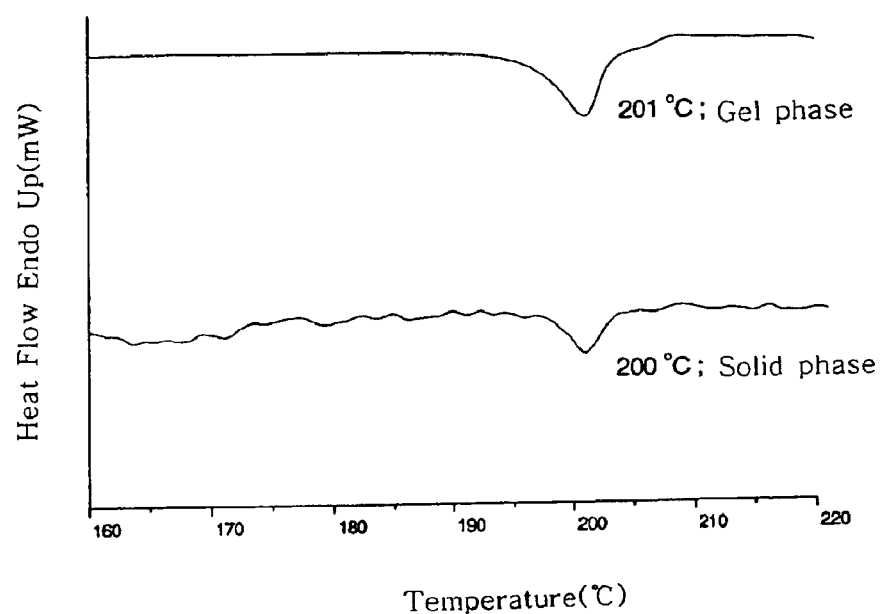
FIG. 3: a differential scanning calorimetry scan of 2'-deoxy-5-[1-((p-ethylphenyl)methyl)-1H-1,2,3-triazol-4-yl]-uridine.

In order to examine the thermal stability of the 2'-deoxyuridine derivative of the present invention, 1 to 4 mg of the derivative prepared in 1-9) was shaped in the form of a pellet, and differential scanning calorimetry was performed therewith at a temperature ranging from 30 to 220° C. The result in FIG. 3 shows that the melting point peak of the solid phase was 200° C., and the gel phase, 201° C., suggesting that the 2'-deoxyuridine derivative of the present invention has good thermal stability.

The 2'-deoxyuridine derivative of the present invention is bioavailable because of its low molecular weight, and forms a gel having satisfactory thermal stability for use as a drug delivery vehicle even at a low concentration.

While the invention has been described with respect to the above specific embodiments, it should be recognized that various modifications and changes may be made to the invention by those skilled in the art which also fall within the scope of the invention as defined by the appended claims.

What is claimed is:

1. A 2'-deoxyuridine derivative of formula I:

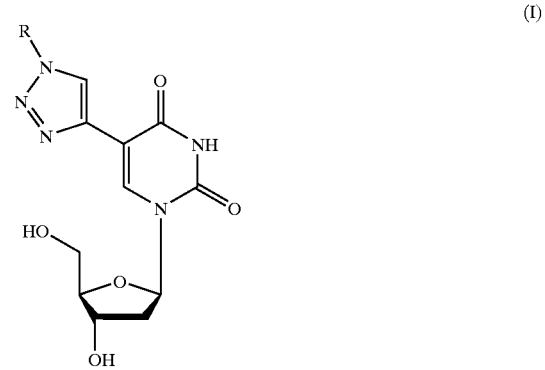

(I)

wherein R is benzyl or substituted benzyl.

2. The derivative of claim 1, wherein R is benzyl having a $C_{1-6}$ alkyl substituent.

3. The derivative of claim 2, wherein R is selected from the group consisting of o-methylbenzyl, m-methylbenzyl, p-methylbenzyl, o-ethylbenzyl, p-ethylbenzyl and p-butylbenzyl.

4. A method for preparing the 2'-deoxyuridine derivatives of claim 1, which comprises the steps of:

1) introducing an acetylene group at the 5-position of 2'-deoxyuridine; and 2) reacting said 2'-deoxyuridine having the acetylene group at the 5-position obtained in step 1) with a benzyl azide derivative.

5. The method of claim 4, wherein the benzyl azide derivative of step 2) is benzyl azide or a $C_{1-6}$ alkylbenzyl azide.

6. The method of claim 5, wherein the $C_{1-6}$ alkylbenzyl azide is selected from the group consisting of o-methylbenzyl azide, m-methylbenzyl azide, p-methylbenzyl azide, o-ethylbenzyl azide, p-ethylbenzyl azide and p-butylbenzyl azide.

7. The method of claim 4, wherein the acetylene group introduced in step 1) is trimethylsilyl ethynyl.

8. The method of claim 4, which further comprises the step of introducing an iodide group at the 5-position of 2'-deoxyuridine, prior to step 1).

9. A hydrogel containing the 2'-deoxyuridine derivative of claim 1.

* * * * *